United States Patent
Davis et al.

(10) Patent No.: US 11,865,237 B2
(45) Date of Patent: Jan. 9, 2024

(54) RADIAL BALLOON CATHETER

(71) Applicant: Surmodics MD, LLC, Eden Prairie, MN (US)

(72) Inventors: Simon Davis, Galway (IE); Michael Reynolds, Eden Prairie, MN (US)

(73) Assignee: Surmodics MD, LLC, Eden Prairie, MN (US)

( * ) Notice: Subject to any disclaimer, the term of this patent is extended or adjusted under 35 U.S.C. 154(b) by 22 days.

(21) Appl. No.: 17/234,206

(22) Filed: Apr. 19, 2021

(65) Prior Publication Data

US 2021/0322732 A1 Oct. 21, 2021

Related U.S. Application Data (60) Provisional application No. 63/012,664, filed on Apr. 20, 2020.

(51) Int. Cl.
| | |
|---|---|
| *A61M 25/10* | (2013.01) |
| *A61M 25/00* | (2006.01) |
| *A61M 25/01* | (2006.01) |

(52) U.S. Cl.
CPC ........ *A61M 25/10* (2013.01); *A61M 25/0054* (2013.01); *A61M 2025/0175* (2013.01); *A61M 2025/1081* (2013.01)

(58) Field of Classification Search
CPC ............ A61M 25/09033; A61M 25/10; A61M 25/0054; A61M 25/0155; A61M 25/0158;
(Continued)

(56) References Cited

U.S. PATENT DOCUMENTS

| | | | |
|---|---|---|---|
| 4,170,996 A | 10/1979 | Wu | |
| 4,921,482 A * | 5/1990 | Hammerslag | A61M 25/0147 604/95.04 |

(Continued)

FOREIGN PATENT DOCUMENTS

| | | |
|---|---|---|
| CN | 115666699 A | 1/2023 |
| JP | 2023522978 | 6/2023 |
| WO | 2021216442 | 10/2021 |

OTHER PUBLICATIONS

"International Application Serial No. PCT US2021 027947, International Search Report dated Aug. 3, 2021", 2 pgs.

(Continued)

*Primary Examiner* — Jason E Flick
*Assistant Examiner* — Justin L Zamory
(74) *Attorney, Agent, or Firm* — Schwegman Lundberg & Woessner, P.A.

(57) ABSTRACT

Disclosed herein are a catheter assembly and method of applying a catheter assembly. In an example, the catheter assembly can include a catheter body and frame member extending between proximal and distal portions, the frame member having a first mechanical characteristic, and a floating sleeve coupled around the frame member and extending between the proximal and distal portions, the floating sleeve having a second mechanical characteristic different than the first mechanical characteristic. The floating sleeve can include at least one floating segment and one or more anchor segments along the catheter body. The at least one floating segment of the floating sleeve can be moveable relative to the frame member, and the one or more anchor segments of the floating sleeve can be interconnected with the frame member.

20 Claims, 6 Drawing Sheets

(58) Field of Classification Search
CPC .......... A61M 25/0147; A61M 25/0043; A61M 25/0136; A61M 25/0144; A61M 2025/0195; A61M 2025/09083; A61M 2025/09133; A61M 2025/0161
See application file for complete search history.

(56) References Cited

U.S. PATENT DOCUMENTS

| | | | |
|---|---|---|---|
| 6,152,912 A * | 11/2000 | Jansen | A61M 25/0053 604/524 |
| 6,228,073 B1 | 5/2001 | Noone et al. | |
| 6,595,989 B1 | 7/2003 | Schaer | |
| 6,626,889 B1 | 9/2003 | Simpson et al. | |
| 6,676,643 B2 | 1/2004 | Brushey | |
| 6,702,782 B2 | 3/2004 | Miller et al. | |
| 6,761,703 B2 | 7/2004 | Miller et al. | |
| 7,070,606 B2 | 7/2006 | Seward | |
| 7,115,134 B2 | 10/2006 | Chambers | |
| 7,115,183 B2 | 10/2006 | Larson et al. | |
| 7,166,100 B2 | 1/2007 | Jordan et al. | |
| 7,309,334 B2 | 12/2007 | Von | |
| 7,708,704 B2 | 5/2010 | Mitelberg et al. | |
| 7,708,755 B2 | 5/2010 | Davis, III et al. | |
| 7,785,317 B2 | 8/2010 | Mitelberg | |
| 7,815,600 B2 | 10/2010 | Al-marashi et al. | |
| 8,012,117 B2 * | 9/2011 | Bonnette | A61M 25/007 604/35 |
| 8,021,351 B2 | 9/2011 | Boldenow et al. | |
| 8,317,715 B2 | 11/2012 | Belleville et al. | |
| 8,323,203 B2 | 12/2012 | Thornton | |
| 8,337,518 B2 | 12/2012 | Nance et al. | |
| 8,454,673 B2 | 6/2013 | Al-marashi et al. | |
| 8,523,841 B2 | 9/2013 | Itou et al. | |
| 8,585,713 B2 | 11/2013 | Ferrera et al. | |
| 8,728,116 B1 | 5/2014 | Janardhan et al. | |
| 8,758,334 B2 | 6/2014 | Coe et al. | |
| 8,771,329 B2 | 7/2014 | Christensen et al. | |
| 8,939,931 B2 | 1/2015 | Von Hoffmann | |
| 9,005,165 B2 | 4/2015 | Kalser et al. | |
| 9,060,784 B2 | 6/2015 | Coe et al. | |
| 9,179,995 B2 | 11/2015 | Janardhan et al. | |
| 9,301,777 B2 | 4/2016 | Silvestro | |
| 9,339,632 B2 | 5/2016 | Eidenschink et al. | |
| 9,372,217 B2 | 6/2016 | Hahl et al. | |
| 9,445,784 B2 | 9/2016 | O'keeffe | |
| 9,616,195 B2 | 4/2017 | Lippert et al. | |
| 9,636,173 B2 | 5/2017 | Goshgarian et al. | |
| 9,692,557 B2 | 6/2017 | Murphy | |
| 9,833,125 B2 | 12/2017 | Stigall et al. | |
| 9,861,727 B2 | 1/2018 | Slager et al. | |
| 9,955,852 B2 | 5/2018 | Kesten et al. | |
| 10,292,573 B2 | 5/2019 | Stigall et al. | |
| 10,315,018 B2 | 6/2019 | Eidenschink et al. | |
| 10,363,389 B2 | 7/2019 | Lippert et al. | |
| 10,434,292 B2 | 10/2019 | Joe et al. | |
| 10,449,334 B2 | 10/2019 | Pillai | |
| 10,561,820 B2 | 2/2020 | Sullivan et al. | |
| 10,568,991 B2 | 2/2020 | Wang et al. | |
| 10,617,847 B2 | 4/2020 | Cottone et al. | |
| 10,687,690 B2 | 6/2020 | Kesten et al. | |
| 10,688,277 B2 | 6/2020 | O'connell et al. | |
| 10,709,312 B2 | 7/2020 | Stigall et al. | |
| 10,980,918 B2 | 4/2021 | Babcock et al. | |
| 11,000,632 B2 | 5/2021 | Babcock et al. | |
| 2001/0049519 A1 | 12/2001 | Holman et al. | |
| 2005/0075661 A1 | 4/2005 | Levine et al. | |
| 2006/0264904 A1 | 11/2006 | Kerby et al. | |
| 2007/0060880 A1 | 3/2007 | Gregorich et al. | |
| 2008/0306441 A1 * | 12/2008 | Brown | A61M 25/10 604/99.01 |
| 2014/0193474 A1 | 7/2014 | Babcock et al. | |
| 2015/0258307 A1 | 9/2015 | Osypka et al. | |
| 2015/0305867 A1 | 10/2015 | Liu et al. | |
| 2015/0374483 A1 | 12/2015 | Janardhan et al. | |
| 2016/0339207 A1 | 11/2016 | Beeckler et al. | |
| 2017/0165001 A1 | 6/2017 | Lyttle | |
| 2017/0296221 A1 | 10/2017 | Di Caprio et al. | |
| 2018/0042743 A1 | 2/2018 | Syed | |
| 2018/0153669 A1 | 6/2018 | Herrera et al. | |
| 2018/0250147 A1 | 9/2018 | Syed | |
| 2019/0298520 A1 | 10/2019 | Cooper et al. | |
| 2020/0016378 A1 | 1/2020 | Williams et al. | |
| 2020/0023164 A1 | 1/2020 | Tran et al. | |
| 2020/0060723 A1 | 2/2020 | Walzman | |
| 2020/0078551 A1 | 3/2020 | Moquin et al. | |
| 2020/0078554 A1 | 3/2020 | Walzman | |
| 2020/0222664 A1 | 7/2020 | Cottone et al. | |
| 2020/0230359 A1 | 7/2020 | Fojtik et al. | |
| 2023/0071144 A1 | 3/2023 | Reynolds et al. | |

OTHER PUBLICATIONS

"International Application Serial No. PCT US2021 027947, Written Opinion dated Aug. 3, 2021", 7 pgs.

"International Application Serial No. PCT/US2021/027947, International Preliminary Report on Patentability dated Nov. 3, 2022", 9 pgs.

"European Application Serial No. 21793660.8, Partial Supplementary European Search Report dated Oct. 19, 2023", 13 pgs.

* cited by examiner

RADIAL BALLOON CATHETER

PRIORITY APPLICATIONS

This application claims the benefit of priority to U.S. Provisional Application Ser. No. 63/012,664, filed Apr. 20, 2020, the content of which is incorporated herein by reference in its entirety.

TECHNICAL FIELD

This document pertains generally, but not by way of limitation, to catheters, or more particularly, to balloon catheters.

BACKGROUND

Catheters are used in a variety of medical procedures to conduct therapeutic or diagnostic functions within a patient. For instance, catheters are used for delivery of medications, fluids, or gases to specified locations in the patient. In other examples catheters conduct diagnostic procedures, withdraw fluids for testing or drain fluids from the patient.

Balloon catheters are a variety of catheter. In some examples, a balloon catheter includes an elongated shaft with an inflatable balloon portion proximate to an end of the shaft. In use, the catheter is inserted and advanced, for instance with a guidewire to position the balloon at a location for treatment (e.g., a diseased vessel). Once inserted, the balloon is expanded to enlarge a restriction, which can be a narrow opening or passage within a body.

OVERVIEW

The present inventors have recognized, among other things, that a problem to be solved includes creating a long, soft catheter that is both flexible and pushable.

A catheter is used in some procedures within long and sometimes tortuous passageways, such as the radial or femoral arteries. Each of the radial or femoral arteries provide access to a variety of locations within the body. For example, the radial artery runs from the wrist toward the eyes. However, the length of the radial artery prohibits the use of ultra-flexible soft catheters without good pushability, as it is difficult to push a soft catheter the length of the radial artery (e.g., 2.5 meters or more). A catheter of this length is long because the passageway is long. Additionally, the radial artery has a lesser diameter than the femoral artery, and is accordingly more difficult to navigate, especially with catheters having lumens, therapeutic elements or the like. To readily and accurately navigate and position such a catheter, a catheter body should be pushable for movement through the vasculature, and also flexible to allow articulation through the vasculature. Pushability and flexibility are, in some examples, inversely proportional. For instance, a pushable catheter body may have decreased flexibility and frustrate articulation. While a flexible catheter body may have decreased pushability and frustrate movement through the vasculature.

The present subject matter provides solutions to these problems with a catheter body having a frame member positioned within a floating sleeve. The frame member includes a material having a first mechanical characteristic, for instance a relatively high modulus of elasticity (a measure of stiffness), such as a metal including stainless steel or the like. The floating sleeve is optionally constructed with a second material and has a second mechanical characteristic. For example, the floating sleeve has a relatively lower modulus of elasticity as its second mechanical characteristic in comparison to the frame member. As described herein, the frame member and floating sleeve cooperatively provide axial stiffness along the length of the catheter body and at the same time provide flexibility for articulation of the catheter body. Thus, the catheter body is readily moved (e.g., pushed) through the body while at the same time the catheter body is curved, bent or the like (e.g., articulated).

In some examples, the frame member is spiral cut. Optionally, the spiral cut of the frame member varies over the length (including portions of the length) of the frame member. The variation in the spiral cut includes, but is not limited to width, pitch or the like and provides variation in mechanical characteristics, such as flexibility, along the length of the frame member. For example, the spiral cut has a relatively larger width and has a shallow pitch (e.g., a flat or acute angle extending similarly to the longitudinal axis of the catheter body) at a proximal portion of the frame member. This arrangement provides enhanced stiffness and corresponding pushability at the proximal portion of the catheter body. Conversely, the spiral cut optionally includes a relatively smaller width and a steeper pitch (e.g., compared to the proximal portion) at the distal portion of the frame member to enhance flexibility.

The frame member floats within the outer floating sleeve. For example, the floating sleeve includes at least one floating segment configured to telescopically articulate or deflect laterally relative to the frame member with deflecting articulation of the catheter body. The floating sleeve optionally includes one or more anchor segments that attach the associated portion of the floating sleeve with a corresponding portion of the frame member. In various examples the anchor segments are interposed between the floating segments, floating segments are interposed between anchor segments, one or more anchor segments are provided at either or both of the proximal or distal portions of the catheter body or the like.

When in use, such as when being applied in a body passageway, pushing the floating sleeve supports and braces the frame member as the catheter body is positioned. When the catheter body is articulated by deflection, bending, or other operator movement, the floating sleeve "floats," and at least the floating segments of the floating sleeve translate relative to the previously corresponding segments of the frame member. The floating sleeve and the frame member move with one or more of telescopic articulation (e.g., relative sliding movement) or lateral deflection to modulate engagement therebetween and corresponding freedom of movement therebetween. In this way, the floating segments telescope or laterally deflect and move relative to the frame member. The freedom of movement provided with this arrangement and localized anchor segments support deflection of the catheter and brace the frame member while permitting deflection and at the same time minimizing stress risers compared to systems having otherwise lengthy bonds (including one or more of length adhesive interfaces, welds, shrink tubing or the like) that may buckle, kink or the like because of stress.

In one example clearance is provided between the frame member and the floating sleeve. For instance, the inner diameter of the floating sleeve is larger than the outer diameter of the frame member. When pushed axially, the frame member and floating sleeve cooperate to provide axial stiffness and the floating sleeve braces the frame member. During articulation of the catheter body, for instance while navigating bends and other tortuous features of the vasculature, clearance facilitates one or more of telescoping movement or lateral deflection of the frame member relative to the floating sleeve. The components deflect differently with lesser interconnecting stress risers (e.g., between a liner bonded with a jacket) that otherwise restrict bending movement. For instance, the floating sleeve in one example is free to bend more drastically than otherwise permitted if the floating sleeve was anchored along the frame member. Continued deflection provides a frictional engagement between the floating sleeve and the frame member that gradually increases (lengthens and provides additional force). The frictional engagement between the components provides a graduated increasing support force (e.g., accordingly to the lengthening of the frictional engagement and increase in friction force) to the catheter body as deflection increases. Accordingly, even when the catheter body is deflected the frictionally engaged floating sleeve and the frame member cooperatively engage to support the catheter body and enhance pushability.

Thus, the assembly of the floating sleeve and the frame member provide one or more of telescoping articulation or lateral deflection therebetween to provide pushability for a catheter while at the same time maintaining supported flexibility. In some examples, the inclusion of one or more features with the frame member, such as helical gaps, spiral cuts, cuts, gaps, scoring or the like or with the floating sleeve including floating segments and anchor segments further enhance flexibility while also ensuring pushability of the catheter. Examples of catheter assemblies having flexibility and pushability by way of the floating assembly are described herein.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The example catheter assemblies described herein are both pushable and flexible for enhanced navigation along passageways including vessels and cavities. The devices and methods discussed herein include a catheter assembly that enhances pushability, resists compression based failure, such as buckling while also providing varying stiffness (and corresponding flexibility) during bending. The catheter assemblies described herein include two or more members, a floating sleeve and a frame member. The two or more members have varying mechanical characteristics in some examples. For instance, the floating sleeve includes a different stiffness characteristic relative to the frame member. In one example, a clearance or tolerance is included between the members to facilitate one or more of lateral and axial movement between the members during deflection while maintaining a cooperative coupling that braces the catheter assembly during pushing. Deflection engages one or more otherwise movable surfaces within floating segments and braces the catheter assembly during deflection, Greater deflection enhances the engagement (e.g., one or more of engagement profile or friction force increases) and correspondingly enhances the bracing of the catheter assembly during the greater deflection. The relative movement and engagement of the catheter assembly components, such as the floating sleeve and the frame member thereby provides enhanced pushability by way of bracing between the floating sleeve and the frame member while at the same time providing enhanced support during deflection through engagement of the otherwise relatively movable components.

Figure 1:
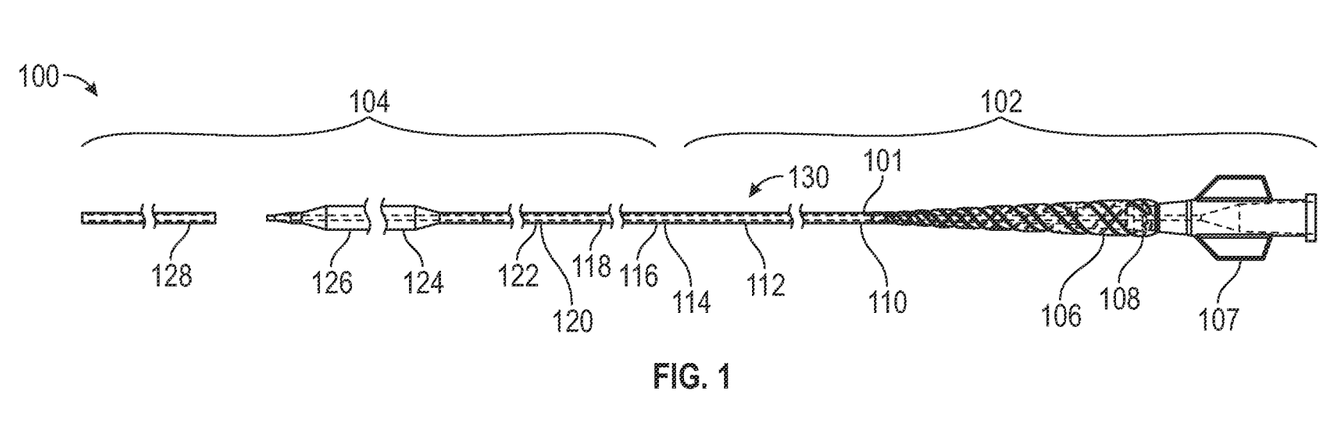
FIG. 1 is a view of one example of a catheter assembly.

FIG. 1 is a view of one example of a catheter assembly 100 having a catheter body 101. The catheter body 101 of the catheter assembly 100 extends between a proximal portion 102 and a distal portion 104. As shown in the FIG. 1, the example catheter assembly 100 includes a strain relief portion 106 and a hub 107. The catheter body 101 of the catheter assembly 100 extends distally from the hub 107 (e.g., through the strain relief portion 106) to the distal portion 104. As described herein, the catheter body 101 includes a floating sleeve 110 surrounding a frame member 130. The floating sleeve 110 is, as described in examples herein, coupled with the frame member 130 at one or more anchor segments while otherwise including floating segments that permit relative movement between the floating sleeve 110 and the frame member 130.

In FIG. 1 the catheter assembly 100 includes a proximal anchor segment 108, a middle anchor segment 116, and distal anchor segment 120. One or more floating segments, such as a proximal floating sleeve segment 112 are interposed between the anchor segments. For instance, the proximal floating sleeve segment 112 is interposed between the proximal and middle anchor segments 108, 116.

In another example, instead of the middle anchor segment 116 the catheter body of FIG. 1 includes a junction 114 that interconnects a distal floating sleeve segment 118 with the proximal floating sleeve segment 112. The distal and proximal floating sleeve segments 112 are interposed between a distal anchor segment 120 and the proximal anchor segment 108.

Figure 2:
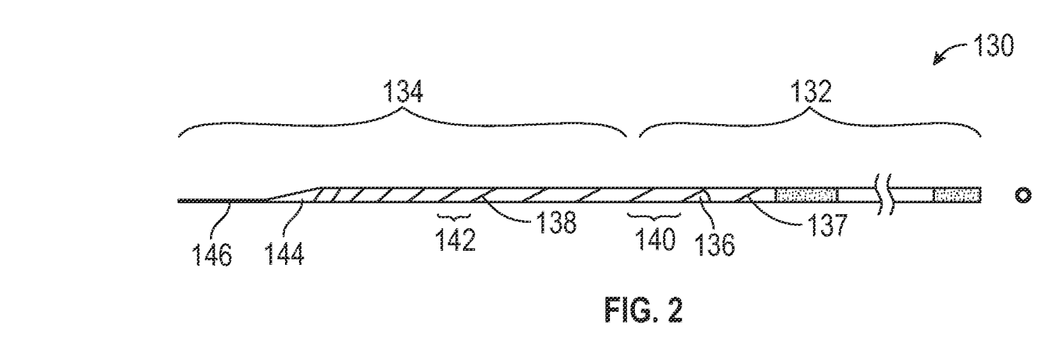
FIG. 2 is a view of one example of a frame member for a catheter assembly.

Referring now to FIG. 2, the frame member 130 of the catheter assembly 100 extends between a proximal portion 132 and a distal portion 134. In one example, the distal portion 134 of the frame member 130 includes an end portion 144 having a skive 146 (e.g., a tapered edge for easier insertion and guiding of the catheter). The frame member 30 in this example includes one or more helical grooves 137 (e.g., cuts, scoring, perforations or the like). For instance, the helical grooves include one or more pitch angles 136, 138, pitch widths 140, 142 or the like to provide specified mechanical characteristics to the various portions of the frame member 130 and corresponding characteristics to the catheter assembly 100. Referring again to FIG. 1, the catheter assembly 100 optionally includes an access port 122 for rapid exchange delivery of the catheter assembly 100. In the example shown in FIG. 1 the present catheter body includes a balloon 124, a balloon protector 126, and a distal tip assembly 128, such as an atraumatic tip. The catheter assembly 100 extends between the proximal portion 102 and the distal portion 104 with the strain relief portion 106 proximate to the proximal portion 102 and the hub 107 (e.g., luer fitting or the like).

In the example shown in FIG. 1 the floating sleeve 110 receives the frame member 130 therein. The floating sleeve 110 includes the proximal floating sleeve segment 112 and the distal floating sleeve segment 118 joined by the floating sleeve junction 114 (e.g., or the anchor segment 116 in another example). The floating sleeve optionally includes a floating segment (decoupled from the frame member 130) that extends from the proximal portion 102 to the distal portion 104. In another example including the anchor segments 108, 116, and 120 the floating sleeve 110 includes the floating segment 112 between the anchor segments 108, 116 and the floating segment 118 between the anchor segments 116, 118. The anchor segments 108, 116, 120 secures the floating sleeve 110 to the frame member 130 while the remainder of the floating sleeve 110 is decoupled from the frame member 130 as described herein. In an example including the access port, the port 122 is proximate to the distal portion 104, for instance near the distal anchor segment 120.

In one example, the catheter body 101 of the assembly 100 has a length of between about 2.0 m to about 4.0 m. The catheter body 101, as described herein, is a component of the catheter assembly 100 having the hub 107 and one or more instruments, catheter instruments, guide catheters, introducers or the like that are delivered through vessels and cavities of a patient, for instance from the leg to the heart or from the wrist to the heart. As described herein the catheter assembly 100 and variations of the same are pushable and flexible.

The catheter assembly 100 may be, for example, a catheter for drainage, administration of fluids or gases, access by surgical instruments, or to perform a variety of other procedures depending on the desired outcome. The strain relief portion 106 resides on or near the proximal portion 102 (e.g., proximate to hub 107) to provide mechanical stress relief to the assembly 100.

The catheter assembly 100 optionally includes a biocompatible coating thereon, such as a hydrophilic coating on an outer surface of the catheter body 101 or the floating sleeve 110 for ease of insertion. The coating can be, for example, a drug coating or a hydrophilic lubricious coating, such as described in U.S. Pat. Nos. 9,861,727, 9,372,217, and U.S. 2014/0193474, which are herein incorporated by reference.

The floating sleeve 110, and outer body, is an outer jacket-like structure in the catheter assembly 100 coupled around the frame member 130 (e.g., covering, partially covering, surrounding, or partially surrounding). The floating sleeve 110 need not be attached to the frame member 130. In an example, there is clearance between the floating sleeve 110 and the frame member 130 to permit relative movement of the frame member 130 and the floating sleeve 110. The floating sleeve 110 has one or more mechanical characteristics including, but not limited to, modulus of elasticity, yield strength, tensile strength hardness, Young's modulus or the like, that varies relative to the corresponding characteristic of the frame member 130. In other examples, the mechanical characteristics of the floating sleeve 110 and the frame member 130 match (e.g., are similar, proximate to each other, are identical or the like).

The floating sleeve 110 optionally includes multiple floating segments alternating with anchor segments. For example, in FIG. 1, two floating segments, the proximal floating sleeve segment 112 and the distal floating sleeve segment 118, are shown, interspersed with three anchor segments: the proximal anchor segment 108, the middle anchor segment 116, and the distal anchor segment 120. The floating sleeve 110 and the anchor segments are interconnected with the frame member 130 to permit relative movement (such as lateral movement, telescoping articulation or the like) of the one or more floating segments of the sleeve 110 relative to the frame member 130.

In one example the proximal floating sleeve segment 112 has a greater mechanical characteristic, such as a higher modulus of elasticity compared to the distal floating sleeve segment 118, and extends along the proximal portion 102 of the catheter assembly 100. The proximal floating sleeve segment 112 is made of, for example, Polyamide 11 or other bioplastics. The floating sleeve junction 114, on or near the middle anchor segment, serves as a juncture between the proximal floating sleeve segment 112 and the distal floating sleeve segment 118. As described herein, in another example the floating sleeve junction 114 includes an intermediate or middle anchor segment 116 that anchors the proximal and distal floating sleeve segments 112, 118 to the frame member 130.

In another example the distal floating sleeve segment 118 has a lower mechanical characteristic, such as a lower modulus of elasticity compared to the proximal floating sleeve segment 112. As such, the distal floating sleeve segment 118 is more flexible than the proximal floating sleeve segment 112. The distal floating sleeve segment 118 is optionally made of an elastic material such as a polyamide 12 elastomer.

The one or more anchor segments are positioned within the catheter assembly 100 to allow attachment of the floating sleeve 110 at specified locations along the catheter assembly 100. The one or more anchor segments secure, fasten, or anchor the floating sleeve 110 to the corresponding portion (or portions) of the frame member 130. In FIG. 1, the proximal anchor segment 108 is optionally positioned beneath the strain relief portion 106, for instance between the floating sleeve 110 and the frame member 130. The anchor segments fix the proximate portions of the sleeve 110 and the frame member 130 at least against relative longitudinal motion in at least one direction (e.g., proximally, distally or both). For example, each anchor segment of the catheter assembly 100 constrains longitudinal motion proximate to the anchor segment in at least one degree of freedom between the floating sleeve 110 and the frame member 130 (e.g., permits unidirectional longitudinal motion while restricting longitudinal motion in a converse direction, or constrains longitudinal motion in multiple directions).

The example middle anchor segment 116 is between the proximal floating sleeve segment 112 and the distal floating sleeve segment 118, for instance proximate to the floating sleeve junction 114. In the example including the middle anchor segment 116 the segment secures the proximate portions of the frame member 130 and the floating sleeve 110. For example, the middle anchor segment 116 arrests relative movement of the proximate portions of the frame member 130 and the floating sleeve 110 in one or more directions (including longitudinal, rotational movements or the like).

The distal anchor segment 120 is between the floating sleeve 110 and the frame member 130 on or near the distal portion 104 of the catheter assembly 100. In the example shown in FIG. 1, the distal anchor segment 120 is proximate the access port 122, such as a rapid exchange access port. In some cases, the distal anchor segment 120 secures (e.g., fastens, anchors or the like) the proximate portion of the frame member 130 to the corresponding portion of the floating sleeve 110. Optionally, the distal anchor segment 120 is integrated with the access port 122. In one example, the distal anchor segment 120 constrains relative movement in one or more degrees of freedom between the associated portions of the floating sleeve 110 and the frame member 130. For instance, the distal anchor segment 120 constrains relative distal movement of the distal portion of the frame member 130 relative to the associated distal portion of the floating sleeve 110. In another example, the distal anchor segment 120 permits proximal relative movement of the distal portion of the frame member 130 relative to the distal portion of the floating sleeve 110.

Although three anchor segments are shown in FIG. 1 in other examples, one or more anchor segments are used. For example, two anchor segments are provided at various locations along the catheter body 101 with one or more associated floating segments for the floating sleeve 110. In another example, one anchor segment is provided along the catheter body 101 and the remainder of the floating sleeve 110 includes one or more floating segments. Anchor segments, floating segments and the like are in various examples used alone, in combination, cooperatively or the like to provide specified mechanical characteristics for the catheter assembly 100. As described herein additional anchor segments and associated floating segments provide enhanced bracing (e.g., support) of the catheter body 101 with initial and greater deflections. In contrast, fewer anchor segments with associated floating segments provide a moderated bracing of the catheter body 101 with initial and greater deflections. As described herein, increased deflection of the catheter body 101 (in each of the configurations discussed above and herein) modulates support provided between the floating sleeve 110 and the frame member 130.

As described herein, relative motion is permitted and guided with the floating segments of the floating sleeve 110. For example, relative motion between the frame member 130 and the floating sleeve 110 occurs along the floating sleeve segments between the anchor segments, such as the proximal anchor segment 108 and the middle anchor segment 116 shown in the example of FIG. 1. During pushing movement, for instance as the catheter assembly 110 is distally moved within a vessel, the floating sleeve 110 and the frame member 130 brace each other because the floating sleeve 110 extends around the frame member 130 and the frame member 130 extends through the floating sleeve 110. The components cooperate to enhance the strength of the catheter body 101 and thereby resist buckling. Additionally, when deflected, the frame member 130 and the floating sleeve 110 progress from an unbound configuration to one or more binding configurations. In the unbound configuration floating segments of the floating sleeve 110 are permitted to move relative to the associated portions of the frame member 130 to lower constraint of deflection caused with fused components (e.g., adhered liners and sleeves, shrunk sleeves on liners or the like). For example, the frame member 130 and the floating sleeve 110 do not fight the movements of each other. With increased deflection the floating segments and the frame member 130 engage and bind with each other (e.g., frictionally) to brace the catheter body 101 of the assembly 100 and support the body during deflection. As described herein, with additional deflection the engagement and binding between the floating segments of the floating sleeve 100 and the frame member 130 increase and the bracing of the catheter body 101 is thereby enhanced in a graduated manner corresponding to the degree of deflection. In this case, the two parts may permit bending or deflection when resisting each other. Engagement and binding between the one or more floating segments of the floating sleeve 110 and the frame member 130 is, as described herein, initiated and graduated with deflection of the catheter body 101. Relative movement between the frame member 130 and the floating sleeve 110 (e.g., proximate to the floating segments) including, but not limited to, sliding, pushing, deflecting, and telescoping movements, as part of deflection of the catheter body 101, initiates and enhances frictional engagement between the components (110 and 130), and the frictional engagement (including static engagement and constrained relative motion) is gradually increased with deflection.

As described herein, anchoring the frame member 130 and the floating sleeve 110 at one or more anchor segments provides additional resistance to relative motion in comparison to frictional engagement alone, at least until frictional engagement with sufficient deflection limits all relative motion. For instance, in the catheter assemblies discussed herein, the proximal anchor segment 108 and the middle anchor segment 116 provide increased stiffness at the proximal portion 102 of the catheter assembly 100 in comparison to the distal portion of the catheter assembly 100. Optionally, the distal anchor segment 120 allows a limited degree of relative movement (e.g., proximal movement of the frame member 130 relative to the sleeve 110) relative to the proximal portion 102 and accordingly provides lesser (initial) stiffness to the distal portion of the catheter assembly 100. Deflection of the catheter assembly 101 and relative motion between the floating sleeve 110 and the frame member 130 are discussed in more detail with regards to FIGS. 3A-5B below.

The access port 122 shown in FIG. 1 is a rapid exchange port for easy access to the frame member 130 when applying or inserting the catheter assembly 100 into a patient cavity or passageway. The access port 122 allows for easy, removal of the frame member 130 or other stiffening wire. Shown in FIG. 1, the frame member 130 terminates in or near the access port 122, such that the frame member 130 does now reach or interact with the balloon 124 or balloon protector 126. In some cases, an additional guide wire may be used in conjunction with the access port 122 for easier movement of the catheter assembly 100.

The balloon 124 is sheltered by the balloon protector 126 to prevent puncture of the balloon 124 prior to or during insertion. The balloon 124 and the balloon protector 126 are coupled with the distal floating sleeve segment 118, in or near the distal portion 104 of the catheter assembly 100. The sub-assembly 128 includes support for the balloon 124 and balloon protector 126, and acts as an insertion tip for the catheter assembly 100. The balloon protector 126 can be removed after or during insertion.

Shown in more detail in FIG. 2, the catheter assembly 100 of FIG. 1 includes the frame member 130, with a proximal portion 132 and a distal portion 134. The frame member 130 may be, for example, a hypotube, a stiffening wire, a braid, coil, inner polymer liner, or the like that enhances pushability and resists buckling. The frame member 130 has a mechanical characteristic, such as modulus of elasticity, yield strength, tensile strength, flexural modulus, hardness, Young's modulus or the like that enhances the strength of the catheter assembly 100. In one example, the frame member 130 has greater strength (e.g., tensile strength or the like) than the floating sleeve 110 while the sleeve 110 is less rigid (e.g., more elastic, flexible or the like).

The frame member 130 extends between the proximal portion 102 and the distal portion 104 of the catheter body 101 of the catheter assembly 100. The frame member 130 is at least partially received within the floating sleeve 110, with optional clearance therebetween. As described herein, the frame member 130 and the floating sleeve 110 are not bonded along the continuous length of the frame member 130, such that the frame member 130 and the floating sleeve 110 may "float" or move relative each other (e.g., along one or more floating segments). In some cases, the frame member 130 is bonded to the floating sleeve 110 at distinct locations, such as one or more anchor segments, and not continuously. The floating configuration of the frame member 130 and the floating sleeve 110 facilitates and controls the variation of mechanical characteristics of the overall catheter assembly 100, such as variations in flexibility and pushability.

In one example, there is be physical clearance between the frame member 130 and the floating sleeve 110 that facilitates lateral and longitudinal movement therebetween. The clearance between them allows for sliding, moving, telescoping, and other motion between the frame member 130 and the floating sleeve 110. For instance, a gap is provided therebetween and represented with variations in the sleeve inner diameter (larger) in comparison to the frame member outer diameter (smaller), In other examples, the frame member 130 and floating sleeve 110 are movably coupled without an affirmative clearance. Instead, the components are permitted to move (e.g., slide, deflect or the like) relative to each other according to pliability in one or more of the components, negligible tolerances (that ensure snug fitting while permitting sliding movement) or the like. Motion between the frame member 130 and the floating sleeve 110 is discussed in more detail with regard to FIGS. 3A-5C below.

As shown in FIG. 2, the frame member 130 is a spiral cut 137 (e.g., scored, full penetration cut, perforations or the like having a helical, slanted or spiral configuration) along its length, from the distal portion 134 to the proximal portion 132. This enhances flexibility near the proximal portion 132 while at the same time maintaining specified rigidity and pushability near the distal portion 134. In one example, the spiral cut 137 is continuous along the length of the frame member 130.

In another example, the configuration of the spiral cut is varied along the frame member 130 (including being absent) to vary mechanical characteristics of the frame member. For instance, as shown in FIG. 2 the pitch angle along the length of the frame member 130 is gradually changed. As shown in FIG. 2, the pitch angle, such as angle 136, can be measured between the spiral cut and the bottom of the frame member 130. Similarly, a pitch width can be measured laterally between two spiral cuts, such as pitch width 142.

In the present example the pitch angle gradually increases (becomes steeper) from the proximal portion 132 to the distal portion 134. For example, in FIG. 2, the first pitch angle 136 is shallower relative to horizontal than the second pitch angle 138. Accordingly, the proximal portion having the shallow pitch angle 136 has enhanced strength and corresponding pushability while the distal portion with the relatively steep second pitch angle 138 has enhanced flexibility to facilitate bending.

Similarly, the pitch width along the length of the frame member 130 gradually becomes narrower from the distal portion 134 to the proximal portion 132, For example, in FIG. 2, the first pitch width 140 is greater than the second pitch width 142. The changing pitch angle and pitch width allows for enhanced flexibility on or near the distal portion 134 of the frame member 130, but increased rigidity and pushability on or near the proximal portion 132 of the frame member 130. In the example shown in FIG. 2, a steeper pitch angle and decreased pitch width can increase flexibility. In contrast, a shallower pitch angle and a greater pitch width can increase strength and pushability.

The end portion 144 and skive 146 resides on or near the distal portion 134 of the frame member 130. With the frame member 130 in the floating sleeve 110, the end portion 144 rests on or near the access port 122. The profile of the end portion 144 in some examples provides a stress riser during deflection of the catheter body 101. In one example, to prevent kinking proximate to the end portion 144 the distal anchor segment 120 (see FIG. 1) can be proximate to the access port 122 and near the end portion 144 of the frame member 130. The distal anchor segment 120 strengthens this location in the catheter assembly 100 (while freeing other portions to float) while lowering stress risers.

The catheter assembly 100 depicted in FIGS. 1 and 2 and including the floating configurations of the sleeve and frame member as described allows transmission of force applied at the proximal portion 102 to the distal portion 104 while lessening buckling, kinking or the like. Additionally, the catheter assembly 100 provides enhanced flexibility and support to the catheter body 101 while deflected with the floating and anchor segments of the floating sleeve 110 and frame member 130. In one example, this is achieved by using radial clearance between the frame member 130 and the floating sleeve 110, such as to induce the parts to act together under compression, and to act separately during bending up to a point where extreme bending causes both the frame member and the floating sleeve 110 to act together. In other examples, lateral relative movement and telescoping movement can be allowed based on clearances.

As such, the catheter assembly 100 has two or more stiffness profiles during bending. For instance, an increased (supporting) stiffness profile and a decreased (flexibility promoting) stiffness profile are provided with the floating sleeve 110 and the frame member 130 cooperatively coupled to allow relative movement. As described herein, the decreased (flexibility promoting) stiffness profile is optionally an initial condition. For instance, as the catheter assembly is navigated through the vasculature the floating segments of the sleeve 110 are movable relative to the frame member 130, and thereby allow the catheter assembly 100 readily deflect (e.g., bend, curve or the like) as it tracks through the vasculature. The floating segments move laterally (e.g., with intervening clearance), longitudinally (e.g., with clearance or sliding engagement) or the like as the catheter assembly tracks through the vasculature and deflects to follow the contour of the vasculature. The relative movement between the frame member 130 and the floating sleeve 110 allows these components to act independently (at least along the floating segments), minimizes binding engagement therebetween and corresponding stress risers (that may cause resistance to travel through vascular geometry, such as buckling or kinking), and permits deflection of the catheter body 101.

In contrast, in an increased (supporting) stiffness profile, such as at a deflected condition greater than the initial (undeflected or lesser deflected) condition, the catheter assembly 100 is resistant to stress induced failure events, such as kinking or buckling that could occur to either segment if they were unsupported. For example, as the catheter body 101 is navigated through relatively more tortuous geometry the catheter body 101 experiences greater deflection and corresponding increased stress. As previously described the floating sleeve 110 having the floating sleeve segments and the frame member 130 are generally permitted to move relative to each other. With increased deflection (e.g., bending or curving) these components engage (as shown in the proceeding Figures). The engagement braces one component with the other, for instance with the friction generated with the engagement. Additionally, the degree of deflection correspondingly changes the engagement interface (increases with greater deflection) between the frame member 130 and the floating sleeve segments thereby also increasing the friction and support provided to the components. The frictional engagement (and gradual increase of the engagement with deflection) provide graduated increasing support between the floating sleeve 110 and the frame member 130 and the components act as one member to resist bending stress applied to the catheter assembly 100.

This type of motion is shown in, and will be discussed in reference to, FIGS. 3A-3D and FIGS. 4A-4D. FIGS. 3A-3D are schematic views of a catheter assembly 300 with one anchor segment 308. FIGS. 4A-4B are schematic views of a catheter assembly 400 with two anchor segments 408, 420. Catheter assembly 300 includes proximal portion 302, distal portion 304, proximal anchor segment 308, floating sleeve 310, and frame member 330. Catheter assembly 400 includes proximal portion 402, distal portion 404, proximal anchor segment 408, floating sleeve 410, distal anchor segment 420, and frame member 430. The assemblies 300, 400, includes components similar to those discussed in reference to FIGS. 1 and 2 above, except where otherwise noted.

Figure 3A:
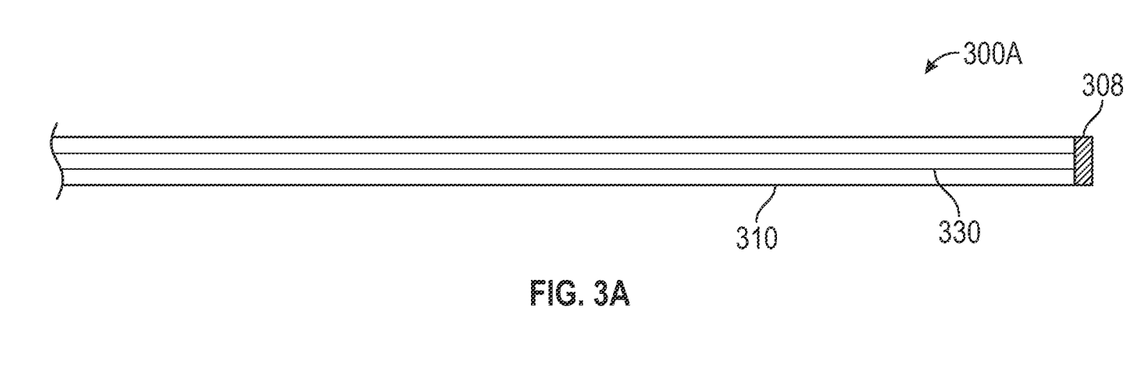
FIG. 3A is a schematic view of a catheter assembly with one anchor segment.
Figure 4A:
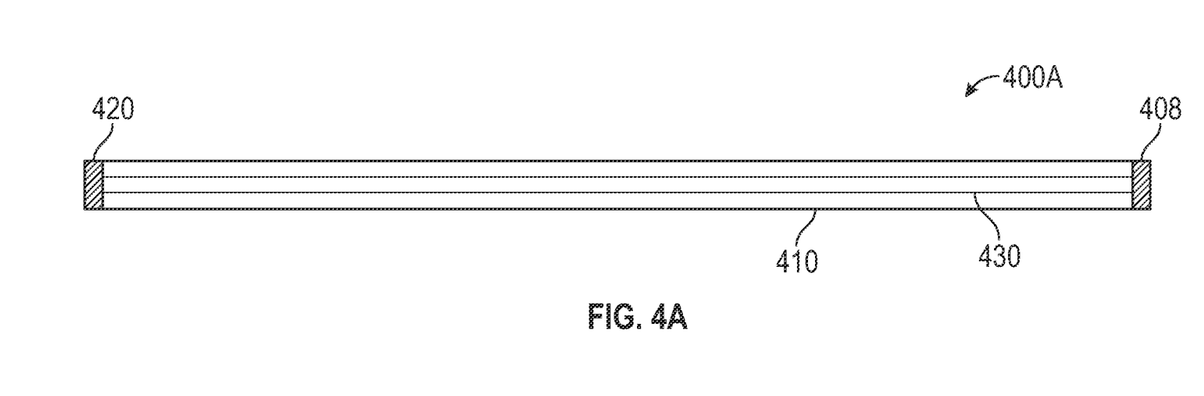
FIG. 4A is a schematic view of a catheter assembly with two anchor segments.
Figure 4B:
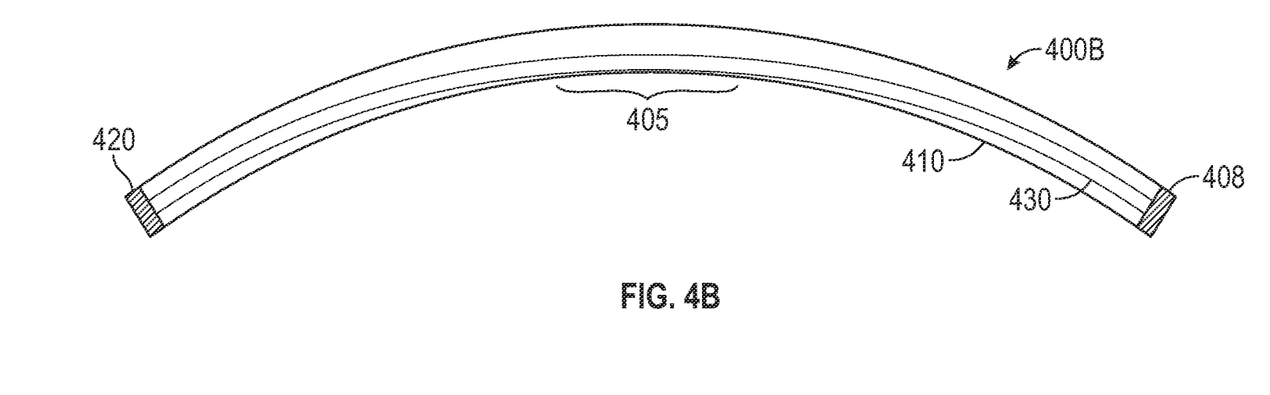
FIG. 4B is a schematic view of a catheter assembly with two anchor segments.

In FIGS. 3A and 4A, the catheter assemblies 300A, 400A are in an initial stiffness profiles, such as at rest, during initial application, or as being applied through minimally tortuous pathways.

Figure 3B:
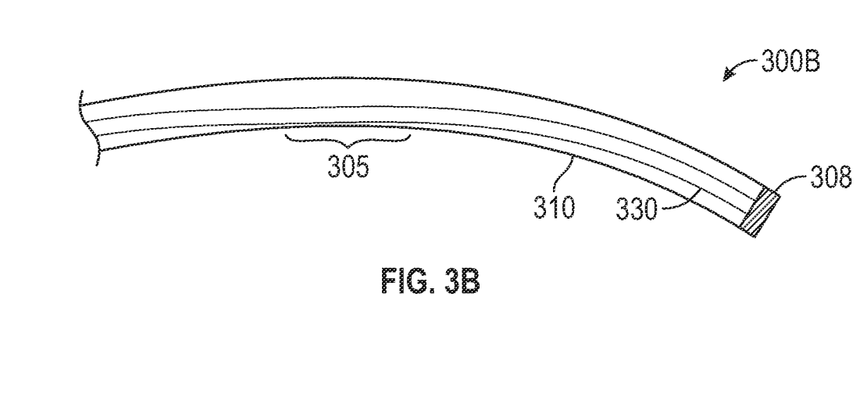
FIG. 3B is a schematic view of a deflected catheter assembly with one anchor segment.

In FIGS. 3B and 4B, the catheter assemblies 300B, 400B, are in a first deflected stiffness profiles, such as during application through a substantially tortuous pathway. Frictional engagement between the floating sleeves (310, 410) and the respective frame members (330, 430) can be seen as section 305, 405.

Figure 3C:
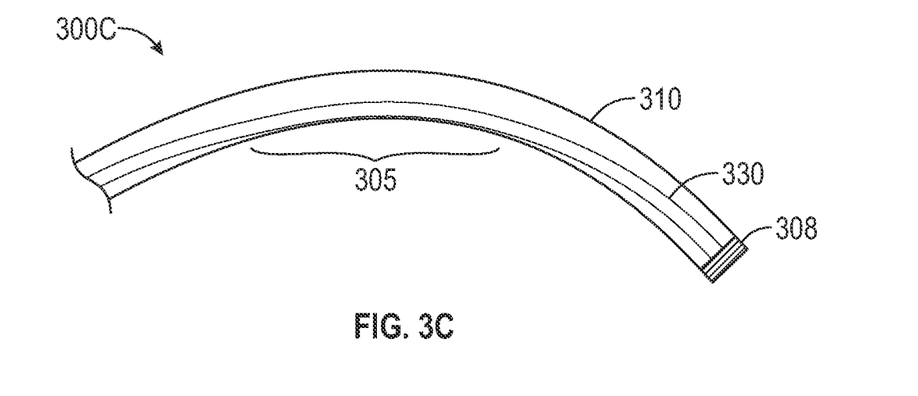
FIG. 3C is a schematic view of a deflected catheter assembly with one anchor segment.
Figure 3D:
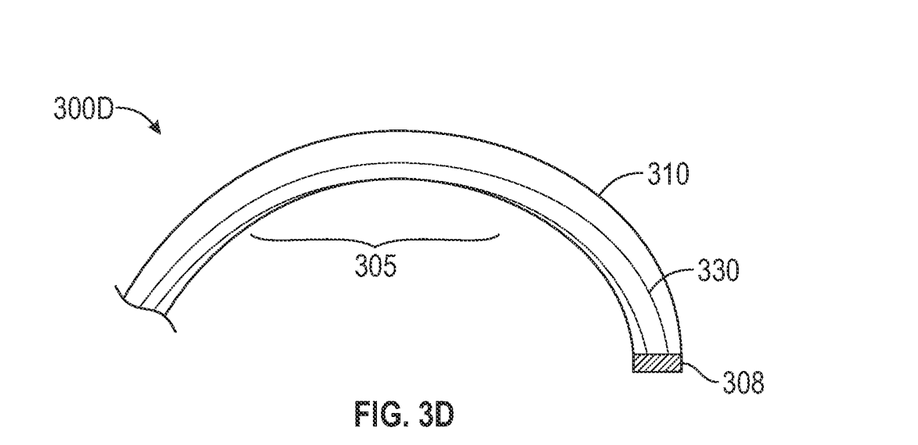
FIG. 3D is a schematic view of a deflected catheter assembly with one anchor segment.
Figure 4C:
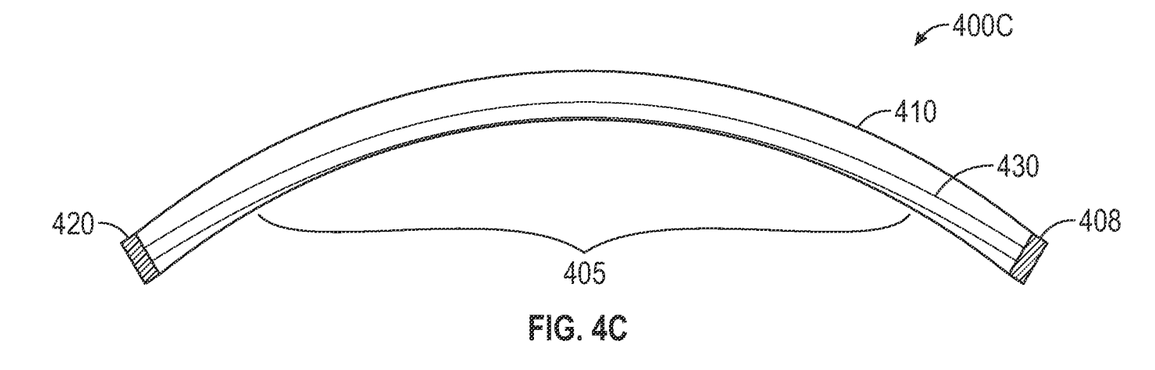
FIG. 4C is a schematic view of a deflected catheter assembly with two anchor segments.
Figure 4D:
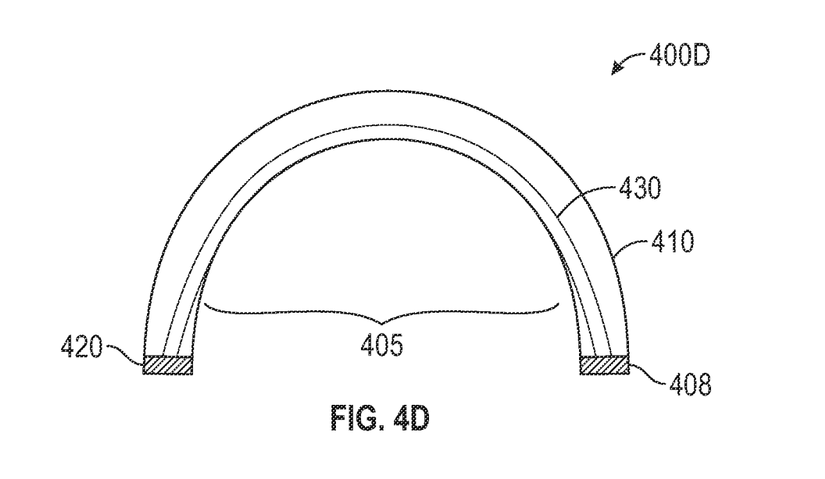
FIG. 4D is a schematic view of a deflected catheter assembly with two anchor segments.

In FIGS. 3C and 4C, the catheter assemblies 300C, 400C, are in a second deflected stiffness profiles, such as during application through a substantially tortuous pathway, that is more deflected than those in FIGS. 3B, 4B. Frictional engagement between the floating sleeves (310, 410) and the respective frame members (330, 430) can be seen as section 305, 405. The frictional engagement area can be larger here compared to in FIGS. 3B, 4B, due to deeper deflection.

In FIGS. 3B and 4B, the catheter assemblies 300B, 400B, are in a first deflected stiffness profiles, such as during application through a substantially tortuous pathway, that is more deflected than those in FIGS. 3C, 4C. Frictional engagement between the floating sleeves (310, 410) and the respective frame members (330, 430) can be seen as section 305, 405. The frictional engagement area can be larger here compared to in FIGS. 3C, 4C, due to deeper deflection.

The clearance between the floating sleeve and the frame member allows for relative movement between the two when deflected. The assembly acts like a bow or rod within a larger tube that engages with the larger tube during deflection sufficient to cause engagement. The clearance provides a gap between frame member and the floating sleeve that is affirmatively bridged during deflection of the device. In contrast, more incident bridging occurs when in the initial non-deflected configuration.

A variety of stress types is applied to the catheter assemblies while being applied, such as buckling, compression, and bending. The catheter assemblies discussed herein resists many of these stresses due to the interaction between the frame member and the floating sleeve.

The frame member and the floating sleeve work together to resist buckling. Resistance to buckling is mathematically defined as:

$$P_{er} = \pi^2 \frac{EI}{(KL)^2}$$

Where $P_{er}$ is the critical longitudinal load (Euler), E is the modulus of elasticity, I is the second moment of area, K is the effective length factor, and L is the unsupported length of the column.

For the catheter assemblies discussed herein, the frame member and the floating sleeve is assembled such that, they are fixed together at least at one end (e.g., FIGS. 3A-3B) or more (e.g., FIGS. 4A-4B). Thus, there would be no relative longitudinal motion between the two components, so the resistance to buckling is described as:

$$P_{er} = \pi^2 \frac{(E_1 I_1 + E_2 I_2)}{(KL)^2}$$

Where $E_1$ is the modulus of elasticity of the frame member, $I_1$ is the second moment of area of the frame member, $E_2$ is the modulus of elasticity of the floating sleeve, and $I_2$ is the second moment of area of the floating sleeve.

Similarly, the frame member and the floating sleeve work together under compressive stress. Compression is mathematically described as:

$$\delta_c = \frac{F}{A_1 + A_2}$$

Where $\delta_c$ is the compressive stress, $A_1$ is the cross sectional area of the frame member, and $A_2$ is the cross sectional area of the floating sleeve. Buckling and compressive stress resistance is increased by increasing the outer diameter of the catheter assembly, which would increase the second moment of inertia (I) and the cross sectional area (A) terms in the above equations.

The catheter assembly further resists bending. Bending stress is described as:

$$\delta_m = \frac{My}{I}$$

Where $\delta_m$ is the bending stress, M is the bending moment, y is the distance to centroidal axis, and I is the second moment of area around the z axis.

The resistance of the catheter assembly to bending stress, e.g., device flexibility, is relative to the second moment of area I, which alternates between a lesser bend and a greater bend as the device bends. Under greater bending conditions, as shown in FIGS. 3B, 4B, the frame member and the floating sleeve is in contact with each other, and the second moments of inertia of the assembly is calculated using the combined radius value. This occurs due to the frictional contact between the outer diameter of the frame member ($r_1$) and the inner diameter of the floating sleeve ($r_2$), which limits or stops relative longitudinal motion between the two members. The second moment of area (I) for an annulus is described as:

$$I = \frac{\pi}{2}(r_2^4 - r_1^4)$$

Where $r_1$ and $r_2$ are the inner and outer radii of the annulus. The larger the difference between the radii, the larger the value of the second moment of area.

When the frame member and the floating sleeve are in contact and relative longitudinal motion is limited (e.g., because of engagement, friction or the like), $r_2$ becomes the outer diameter of the floating sleeve, and $r_1$ becomes the inner diameter of the frame member. Under greater bending conditions, the second moment of area (I) is larger, ensuring the assembly has a larger resistance to bending stress, thus, resistance to kinking.

At lesser bending conditions, both the frame member and the floating sleeve independently move relative each other as the device bends. As such, the second moments of area of both the frame member and the floating sleeve may not act in combination. When the assembly is under bending stress but not at larger bending stress, the bending stress in the assembly occurs at the outer diameter of the floating sleeve, as the distance to the centroidal axis is extended. Additionally, the second moment of area (I) of the frame member acts independently, without support from the outer member. Lower bending stress occurs at the outer diameter of the frame member, as the distance from the centroidal axis is low compared to the floating sleeve. The second moment of area (I) of the floating sleeve acts independently from the frame member.

A flexibility profile (e.g., a flexibility range) of the catheter assembly is based on the smaller and larger bending conditions. As bending stress is applied to the catheter assembly, contact between the frame member and the floating sleeve begins to occur. As bending stress increases, so does the area of surface contact and the force acting on this surface area. As surface contact and force between the frame member and the floating sleeve increases, so too does friction force. Based on this, the stiffness of the catheter assembly increases as bending stress increases. This provides a smooth transition from non-stiff to stiff condition in relation to the bending stress applied to the catheter assembly during use.

FIGS. 3A-3D depict a catheter assembly 300 with one anchor segment 308, while FIGS. 4A-4D depict a catheter assembly 400 with two anchor segments, 408, 420. Additional anchor segments provide more stiffness from the outset that minimizes the use of friction to provide engagement between the floating sleeve and the frame member during deflection. Conversely, a lesser number of anchor segments facilitate flexibility and rely on frictional engagement with greater deflection of the catheter assembly. The number and placement of anchor segments may be chosen and tuned to achieve specific characteristics that rise and lower with deflection.

As the catheter assembly deflects more, the point of contact between the frame member and the floating sleeve grows as a larger area of each comes into contact with the other. As deflection increases, the point of contact lengthens and accordingly provide additional friction force to brace one component against the other as a function of length and normal force that increases due to deflection.

Figure 5A:
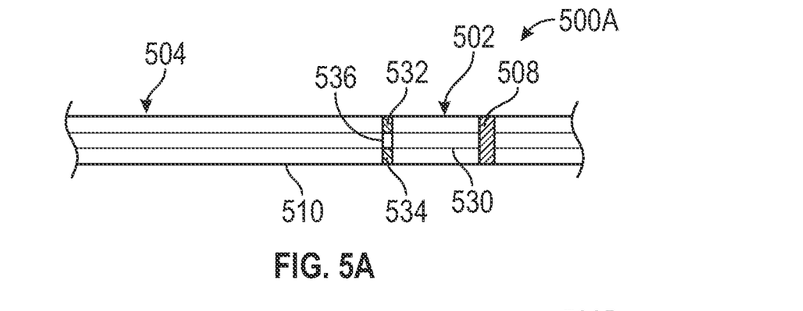
FIG. 5A is a schematic view of a catheter assembly moving in a telescoping articulation.
Figure 5B:
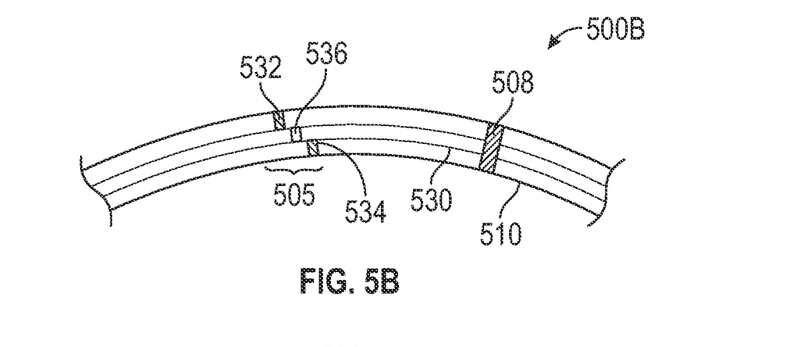
FIG. 5B is a schematic view of a deflected catheter assembly moving in a telescoping articulation.
Figure 5C:
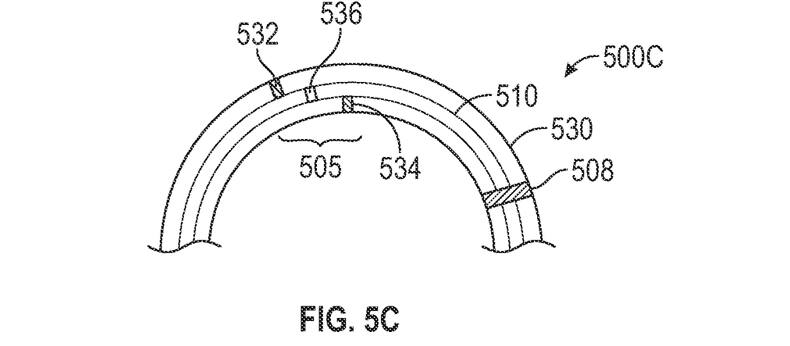
FIG. 5C is a schematic view of a deflected catheter assembly moving in a telescoping articulation.

FIGS. 5A-5C are schematic views of a catheter assembly 500 moving in a telescoping articulation, such as sliding with no or minimal tolerance. The catheter assembly 500 includes a proximal portion 502, a distal portion 504, an anchor point 508, a floating sleeve 510, and a frame member 530. In the catheter assembly 500, two indexed locations 532, 534, are shown to illustrate telescoping movement of the frame member 510 within the floating sleeve 530.

The frame member 530 and the floating sleeve 510 interact with each other in a lesser manner when in an initial non-deflected condition as shown in FIG. 5A, and in a greater manner in a deflected condition such as shown in FIGS. 5B and 5C. This may be achieved with sliding members, where increasing friction during deflection causes the two members to complement each other's resistance to bending. The floating sleeve is articulable over the frame member 530 during application of the catheter assembly 500.

In assembly 500, as the catheter assembly deflects, the frame member 530 and the floating sleeve 510 are engaged immediately or near immediately at frictional engagement section 505. The frame member 530 and the floating sleeve 510 may initially slide over each other with enhanced flexibility, but deflection initiates an engagement between the surfaces of the two and immediate application of friction therebetween. Friction increases with deflection (e.g., as one or more of the normal force and sized of the surfaces engaged increases). The frictional engagement 505 of the floating sleeve 510 against the frame member can increase (e.g., lengthen) with increased deflection, shown in FIG. 5C compared to FIGS. 5A and 5B. The catheter assembly 500 has a varied flexibility and strength profile along the length of the catheter assembly 500. For example, flexibility is initially high because of minimal frictional engagement. As deflection occurs flexibility trends down. Conversely, mechanical strength increases because of the frictional engagement 505 as deflection occurs (and frictional engagement increases with greater deflection) to support the catheter assembly 500 and thereby minimize complications, such as kinking or the like.

In some cases, the assembly 500 may additionally include one or more anchor segments. For instance, the frame member 530 could be anchored at one end, such as in the proximal portion 502, while slidably coupled along the remainder of the interface between the frame member 530 and the floating sleeve 510, In this case, the catheter assembly could be slidably engaged between the frame member 530 and the floating sleeve 510.

Anchoring the frame member 530 and the floating sleeve 510 at some points, and using friction between the frame member 530 and the floating sleeve 510 are complimentary methods of achieving a stiffness profile across a device. Both methods are limiting relative motion between the frame member 530 and the floating sleeve 510, and this limited relative motion may change the overall stiffness of the two combined members.

Figure 6:
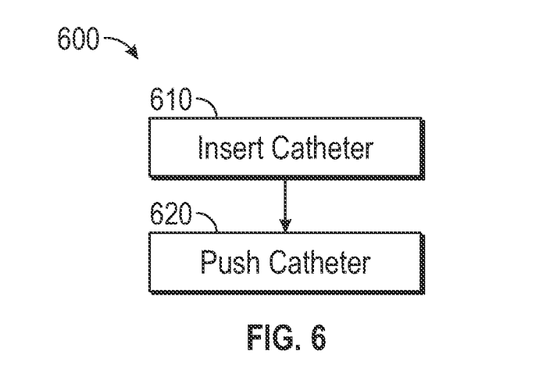
FIG. 6 is a block diagram depicting a method of using a catheter assembly.

FIG. 6 is a diagram depicting an example method 600 of applying a catheter assembly. The method includes steps 610 to 620. In step 610, the catheter assembly is inserted into a passageway, such as in a patient. The catheter assembly includes a frame member and a floating sleeve coupled around the frame member. The frame member and the floating sleeve has differing mechanical characteristics.

In step 620, the catheter assembly is pushed and guided towards the goal position within the passageway. Pushing and guiding the catheter assembly includes telescopically articulating the floating sleeve relative to the frame members.

In some cases, the floating sleeve includes one or more floating sleeve segments interspersed with one or more anchor segments. In this case, pushing the catheter includes telescopically articulating the one or more floating segments relative the frame member.

VARIOUS NOTES AND ASPECTS

Aspect 1 can include a catheter assembly such as can include a catheter body extending between a proximal portion and a distal portion. The catheter body includes a frame member extending between the proximal and distal portions, the frame member having a first mechanical characteristic, and a floating sleeve coupled around the frame member and extending between the proximal and distal portions, the floating sleeve having a second mechanical characteristic different than the first mechanical characteristic. The floating sleeve includes at least one floating segment and one or more anchor segments along the catheter body. The at least one floating segment of the floating sleeve is moveable relative to the frame member, and the one or more anchor segments of the floating sleeve are interconnected with the frame member.

Aspect 2 can include, or can optionally be combined with the subject matter of Aspect 1, to optionally include a catheter assembly wherein the catheter body includes initial and deflected configurations: in the initial configuration in the deflected configuration the catheter body is deflected relative to the initial configuration, and at least a portion of the floating segment is frictionally engaged with the frame member according to the degree of deflection.

Aspect 3 can include, or can optionally be combined with the subject matter of Aspect 1, to optionally include a catheter assembly, wherein the at least one floating segment of the floating sleeve is telescopically articulable.

Aspect 4 can include, or can optionally be combined with the subject matter of Aspect 1, to optionally include a catheter assembly, wherein the first or second mechanical characteristic includes at least one of yield strength, tensile strength, hardness, young's modulus.

Aspect 5 can include, or can optionally be combined with the subject matter of Aspect 1, to optionally include a catheter assembly, further comprising clearance between the floating sleeve and the frame member.

Aspect 6 can include, or can optionally be combined with the subject matter of Aspect 1, to optionally include a catheter assembly, wherein the frame member is slidable within the floating sleeve.

Aspect 7 can include, or can optionally be combined with the subject matter of Aspect 1, to optionally include a catheter assembly, wherein the frame member comprises a hypo-tube.

Aspect 8 can include, or can optionally be combined with the subject matter of Aspect 1, to optionally include a catheter assembly, wherein the frame member comprises a stiffening wire.

Aspect 9 can include, or can optionally be combined with the subject matter of Aspect 1, to optionally include a catheter assembly, wherein the frame member comprises a braid or coil.

Aspect 10 can include, or can optionally be combined with the subject matter of Aspect 1, to optionally include a catheter assembly, wherein the frame member comprises an inner polymer liner.

Aspect 11 can include, or can optionally be combined with the subject matter of Aspect 1, to optionally include a catheter assembly, wherein the frame member is configured to allow pushing of the catheter assembly.

Aspect 12 can include, or can optionally be combined with the subject matter of Aspect 1, to optionally include a catheter assembly, wherein the floating sleeve comprises a distal floating sleeve segment and a proximal floating sleeve segment.

Aspect 13 can include, or can optionally be combined with the subject matter of Aspect 12, to optionally include a catheter assembly, wherein the distal floating sleeve segment comprises a is less rigid than the proximal distal segment.

Aspect 14 can include, or can optionally be combined with the subject matter of Aspect 12, to optionally include a catheter assembly, wherein the floating sleeve further comprises a junction joining the distal floating sleeve segment and the proximal floating sleeve segment.

Aspect 15 can include, or can optionally be combined with t subject matter of Aspect 1, to optionally include a catheter assembly, wherein the frame member comprises a spiral cut.

Aspect 16 can include, or can optionally be combined with the subject matter of Aspect 15, to optionally include a catheter assembly, wherein the spiral cut comprises a continuous cut around an external surface of the frame member.

Aspect 17 can include, or can optionally be combined with the subject matter of Aspect 15, to optionally include a catheter assembly, wherein the spiral cut comprises a first pitch angle and second pitch angle, the second pitch angle being lesser than the first pitch angle.

Aspect 18 can include, or can optionally be combined with the subject matter of Aspect 17, to optionally include a catheter assembly, wherein the spiral cut gradually changes from the first pitch angle to the second pitch angle along the frame member from the distal portion of the assembly to the proximal portion of the assembly.

Aspect 19 can include, or can optionally be combined with the subject matter of Aspect 15, to optionally include a catheter assembly, wherein the spiral cut comprises a first pitch width and second width angle, the second width angle being larger than the first pitch width.

Aspect 20 can include, or can optionally be combined with the subject matter of Aspect 19, to optionally include a catheter assembly, wherein the spiral cut gradually changes from the first pitch width to the second pitch width along the frame member from the distal portion of the assembly to the proximal portion of the assembly.

Aspect 21 can include, or can optionally be combined with the subject matter of Aspect 19, to optionally include a catheter assembly, wherein the one or more anchor segments include a first anchor segment near the proximal portion of the assembly, a second anchor segment between the proximal portion of the assembly and the distal portion of the assembly, and a third anchor segment near the distal end of the assembly.

Aspect 22 can include, or can optionally be combined with the subject matter of Aspect 21, to optionally include a catheter assembly, wherein the first, second, and third anchor segments allow for motion of the frame member within the floating sleeve therebetween.

Aspect 23 can include, or can optionally be combined with the subject matter of Aspect 1, to optionally include a catheter assembly, further comprising a rapid exchange port on the distal portion of the assembly.

Aspect 24 can include, or can optionally be combined with the subject matter of Aspect 1, to optionally include a catheter assembly, wherein the assembly has a length of about 2.0 m to about 4.0 m.

Aspect 25 can include, or can optionally be combined with the subject matter of Aspect 1, to optionally include a catheter assembly, wherein the assembly has a length of about 2.5 m to about 3.5 m.

Aspect 26 can include, or can optionally be combined with the subject matter of Aspect 1, to optionally include a catheter assembly, further comprising a guidewire for applying the catheter assembly.

Aspect 27 can include a catheter assembly such as can include a catheter body extending between a proximal portion and a distal portion. The catheter body can include a frame member extending between the proximal and distal portions, the frame member having a first mechanical characteristic, and a floating sleeve coupled around the frame member and extending between the proximal and distal portions, the floating sleeve having a second mechanical characteristic different than the first mechanical characteristic, wherein the floating sleeve is configured to move relative the frame member. The catheter body is configured for deflection between initial and deflected configurations: in the initial configuration the floating sleeve and the frame member cooperatively support the catheter assembly; and in the deflected configuration the floating segment frictionally engages with the frame member according to a degree of deflection, and the frictional engagement supports the catheter assembly according to the degree of deflection.

Aspect 28 can include, or can optionally be combined with the subject matter of Aspect 27, to optionally include a catheter assembly, wherein the first or second mechanical characteristic includes at least one of yield strength, tensile strength, hardness, young's modulus.

Aspect can include, or can optionally be combined with the subject matter of Aspect 27, to optionally include a catheter assembly, wherein the catheter body is configured to be pushed as it is deflected between the initial configuration and the deflected configuration.

Aspect 30 can include, or can optionally be combined with the subject matter of Aspect 27, to optionally include a catheter assembly, wherein the initial configuration includes clearance between the floating segment and the corresponding segment of the frame member.

Aspect 31 can include a method of applying a catheter assembly, such as can include inserting a catheter assembly into a passageway, the catheter assembly including a frame member and a floating sleeve coupled around the frame member, wherein the frame member and the floating sleeve are movable relative to each other; navigating the catheter assembly along the passageway toward a specified position, wherein navigating the catheter assembly includes: pushing the catheter assembly from a proximal catheter end, wherein the floating sleeve and the frame member cooperatively support the catheter assembly; and deflecting the catheter assembly into a deflected configuration, wherein the floating sleeve frictionally engages with the frame member according to a degree of deflection, and the frictional engagement supports the catheter assembly according to the degree of deflection.

Aspect 32 can include, or can optionally be combined with the subject matter of Aspect 27, to optionally include a method, wherein the floating sleeve includes one or more floating segments divided by one or more anchor segments.

Aspect 33 can include, or can optionally be combined with the subject matter of Aspect 27, to optionally include a method, wherein pushing the catheter assembly comprises telescopically articulating the one or more floating segments relative the frame member.

Aspect 34 can include, or can optionally be combined with the subject matter of Aspect 27, to optionally include a method, further comprising guiding the catheter assembly with a guide wire.

Aspect 35 can include, or can optionally be combined with the subject matter of Aspect 27, to optionally include a method, further comprising articulating the catheter assembly through a rapid exchange port.

Each of these non-limiting aspects can stand on its own or can be combined in various permutations or combinations with one or more of the other aspects.

The above description includes references to the accompanying drawings, which form a part of the detailed description. The drawings show, by way of illustration, specific embodiments in which the invention can be practiced. These embodiments are also referred to herein as "aspects" or "examples." Such aspects or example can include elements in addition to those shown or described. However, the present inventors also contemplate aspects or examples in which only those elements shown or described are provided. Moreover, the present inventors also contemplate aspects or examples using any combination or permutation of those elements shown or described (or one or more features thereof), either with respect to a particular aspects or examples (or one or more features thereof), or with respect to other Aspects (or one or more features thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first,"

"second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described aspects or examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim, Rather, inventive subject matter may lie in less than all features of a particular disclosed embodiment. Thus, the following claims are hereby incorporated into the Detailed Description as aspects, examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A catheter assembly comprising:
   a catheter body extending distally from a position proximate to a hub of the catheter assembly into a distal portion, the distal portion having an end portion, the catheter body includes:
   a frame member extending between the proximal and distal portions, and proximal to the end portion, the frame member having a first mechanical characteristic; and
   a floating sleeve coupled around the frame member and extending between the proximal and distal portions, and proximal to the end portion, the floating sleeve having a second mechanical characteristic different than the first mechanical characteristic;
   wherein the floating sleeve includes at least one floating segment and one or more anchor segments along the catheter body;
   wherein the at least one floating segment of the floating sleeve is moveable relative to the frame member, and the one or more anchor segments of the floating sleeve are interconnected with the frame member.

2. The catheter assembly of claim 1, wherein the catheter body includes initial and deflected configurations:
   in the initial configuration the floating sleeve and the frame member cooperatively support the catheter assembly,
   in the deflected configuration the catheter body is deflected relative to the initial configuration, and at least a portion of the floating sleeve is frictionally engaged with the frame member according to the degree of deflection.

3. The catheter assembly of claim 1, wherein the at least one floating segment of the floating sleeve is telescopically articulable.

4. The assembly of claim 1, further comprising clearance between the floating sleeve and the frame member.

5. The assembly of claim 1, wherein the frame member is slidable within the floating sleeve.

6. The assembly of claim 1, wherein the frame member comprises a hypo-tube, a stiffening wire, a braid, a coil, an inner polymer liner, or combinations thereof.

7. The assembly of claim 1, wherein the floating sleeve comprises a distal floating sleeve segment and a proximal floating sleeve segment, and wherein the distal floating sleeve segment a is less rigid than the proximal distal segment.

8. The assembly of claim 7, wherein the floating sleeve further comprises a junction joining the distal floating sleeve segment and the proximal floating sleeve segment.

9. The assembly of claim 1, wherein the frame member comprises a spiral cut comprising a continuous cut around an external surface of the frame member.

10. The assembly of claim 9, wherein the spiral cut comprises a first pitch angle and second pitch angle, the second pitch angle being lesser than the first pitch angle, and wherein the spiral cut gradually changes from the first pitch angle to the second pitch angle along the frame member from the distal portion of the assembly to the proximal portion of the assembly.

11. The assembly of claim 9, wherein the spiral cut comprises a first pitch width and second width angle, the second width angle being larger than the first pitch width, and wherein the spiral cut gradually changes from the first pitch width to the second pitch width along the frame member from the distal portion of the assembly to the proximal portion of the assembly.

12. The assembly of claim 1, wherein the one or more anchor segments include a first anchor segment near the proximal portion of the assembly, a second anchor segment between the proximal portion of the assembly and the distal portion of the assembly, and a third anchor segment near the distal end of the assembly.

13. The assembly of claim 12, wherein the first, second, and third anchor segments allow for motion of the frame member within the floating sleeve therebetween.

14. The assembly of claim 1, further comprising a rapid exchange port on the distal portion of the assembly.

15. A catheter assembly comprising:
    a catheter body extending distally from a position proximate to a hub of the catheter assembly and between the catheter body having a proximal portion and a distal portion, the catheter body includes:
    a frame member extending between the proximal and distal portions, the frame member having a first mechanical characteristic; and
    a floating sleeve coupled around the frame member and extending between the proximal and distal portions, the floating sleeve having a second mechanical characteristic different than the first mechanical characteristic, wherein the floating sleeve is configured to move relative the frame member;
    wherein the catheter body is configured for deflection between initial and deflected configurations:

in the initial configuration the floating sleeve and the frame member cooperatively support the catheter assembly; and in the deflected configuration the floating sleeve frictionally engages with the frame member according to a degree of deflection, and the frictional engagement supports the catheter assembly according to the degree of deflection.

16. The catheter assembly of claim 15, wherein the catheter body is configured to be pushed as it is deflected between the initial configuration and the deflected configuration.

17. The catheter assembly of claim 15, wherein the initial configuration includes clearance between the floating sleeve and a corresponding segment of the frame member.

18. A method of applying a catheter assembly, comprising:

inserting the catheter assembly into a passageway, the catheter assembly including:

a frame member and a floating sleeve coupled around the frame member;

wherein the frame member and the floating sleeve are movable relative to each other;

navigating the catheter assembly along the passageway toward a specified position, wherein navigating the catheter assembly includes:

pushing the catheter assembly from a proximal catheter end, wherein the floating sleeve and the frame member cooperatively support the catheter assembly; and deflecting the catheter assembly into a deflected configuration, wherein the floating sleeve frictionally engages with the frame member according to a degree of deflection, and the frictional engagement supports the catheter assembly according to the degree of deflection.

19. The method of claim 18, wherein the floating sleeve includes one or more floating segments divided by one or more anchor segments, and wherein pushing the catheter assembly comprises telescopically articulating the one or more floating segments relative the frame member.

20. The method of claim 18, further comprising articulating the catheter assembly through a rapid exchange port.

* * * * *